(12) United States Patent
Wang et al.

(10) Patent No.: US 10,213,110 B2
(45) Date of Patent: Feb. 26, 2019

(54) ANALYSIS OF OPTICAL TOMOGRAPHY (OCT) IMAGES

(71) Applicant: CASE WESTERN RESERVE UNIVERSITY, Cleveland, OH (US)

(72) Inventors: Zhao Wang, Quincy, MA (US); Andrew M. Rollins, Highland Heights, OH (US); David L. Wilson, Cleveland Heights, OH (US); Hiram G. Bezerra, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 464 days.

(21) Appl. No.: 15/007,769

(22) Filed: Jan. 27, 2016

(65) Prior Publication Data

US 2016/0213253 A1 Jul. 28, 2016

Related U.S. Application Data

(60) Provisional application No. 62/108,408, filed on Jan. 27, 2015.

(51) Int. Cl.
| | |
|---|---|
| *A61B 5/05* | (2006.01) |
| *A61B 5/00* | (2006.01) |
| *G06T 7/00* | (2017.01) |
| *A61B 5/145* | (2006.01) |
| *A61B 1/04* | (2006.01) |
| *A61B 5/1455* | (2006.01) |

(Continued)

(52) U.S. Cl.
CPC ............ *A61B 5/0066* (2013.01); *A61B 1/043* (2013.01); *A61B 5/0071* (2013.01); *A61B 5/0084* (2013.01); *A61B 5/02007* (2013.01); *A61B 5/145* (2013.01); *A61B 5/14539* (2013.01); *A61B 5/14556* (2013.01); *G06T 7/0012* (2013.01); *A61B 5/6852* (2013.01); *A61B 2034/2055* (2016.02); *A61B 2576/02* (2013.01); *A61F 2/82* (2013.01); *G06T 2207/30052* (2013.01)

(58) Field of Classification Search
None
See application file for complete search history.

(56) References Cited

U.S. PATENT DOCUMENTS

| | | | |
|---|---|---|---|
| 8,831,321 B1 * | 9/2014 | Elbasiony | A61B 5/0066 382/131 |
| 2007/0167710 A1 * | 7/2007 | Unal | A61B 5/0066 600/407 |

(Continued)

OTHER PUBLICATIONS

Tsantis ("Automatic vessel lumen segmentation and stent strut detection in intravascular optical coherence tomography", Med. Phys. 39(1), Jan. 2012).*

(Continued)

*Primary Examiner* — Jonathan Cwern
(74) *Attorney, Agent, or Firm* — Tarolli, Sundheim, Covell & Tummino LLP

(57) ABSTRACT

A method includes storing three-dimensional image data acquired intravascularly via an optical coherence tomography (OCT) apparatus. The image data is analyzed to compute a probability estimate of stent presence at support positions appearing in an A-line. Stent strut locations are located in three-dimensional space based on the computed probability estimate of stent presence.

25 Claims, 9 Drawing Sheets

(51) Int. Cl.
A61B 5/02 (2006.01)
A61B 34/20 (2016.01)
A61F 2/82 (2013.01)

(56) References Cited

U.S. PATENT DOCUMENTS

| | | | |
|---|---|---|---|
| 2010/0094127 A1* | 4/2010 | Xu | A61B 5/0066 600/425 |
| 2011/0182517 A1* | 7/2011 | Farsiu | A61B 5/0066 382/190 |
| 2012/0075638 A1* | 3/2012 | Rollins | A61B 1/00009 356/479 |
| 2013/0261446 A1* | 10/2013 | Paladini | A61B 5/0064 600/436 |
| 2014/0100449 A1* | 4/2014 | Begin | A61B 8/0841 600/424 |
| 2014/0218740 A1* | 8/2014 | Nebosis | A61B 5/0066 356/479 |

OTHER PUBLICATIONS

Mandelias ("Automatic quantitative analysis of in-stent restenosis using FD-OCT in vivo intra-arterial imaging", Med. Phys. 40(6), Jun. 2013).*

Lu ("Automatic stent detection in intravascular OCT images using bagged decision trees", Biomedical Optics Express, vol. 3, No. 11, Nov. 2012).*

Bland, et al., "Statistical Methods for Assessing Agreement Between Two Methods of Clinical Measurement", The Lancet, vol. 327, No. 8476, pp. 307-310, 1986.

Bezerra, et al., "Intracoronary Optical Coherence Tomography: A Comprehensive Review: Clinical and Research Applications", JACC Cardiovasc Interv. Nov. 2009 ; 2(11): 1035-1046.

Bonnema, et al., "An automatic algorithm for detecting stent endothelialization from volumetric optical coherence tomography datasets", Phys. Med. Biol. 53 (2008), pp. 3083-3098.

Bouma, et al., "Evaluation of intracoronary stenting by intravascular optical coherence tomography", Heart, vol. 89, No. 3, pp. 317-320, Mar. 1, 2003.

Boykov, et al., "Interactive Graph Cuts for Optimal Boundary & Region Segmentation of Objects in N-D Images", Proc. Int'l Conf. Computer Vision, pp. 105-112, 2001.

Boykov, et al., "An Experimental Comparison of Min-Cut/Max-Flow Algorithms for Energy Minimization in Vision", IEEE Transactions on Pattern Analysis and Machine Intelligence, vol. 26, No. 9, Sep. 2004.

Boykov, et al., "Graph Cuts and Efficient N-D Image Segmentation", International Journal of Computer Vision 70(2), 109-131, 2006.

Camenzind, et al., "Stent Thrombosis Late After Implantation of First-Generation Drug-Eluting Stents", Circulation, vol. 115, No. 11, pp. 1440-1455, Mar. 20, 2007.

Chalan, et al., "A Methodology for Evaluation of Boundary Detection Algorithms on Medical Images", IEEE Transactions on Medical Imaging, vol. 16, No. 5, Oct. 1997.

Chamie, et al., "Three-Dimensional Fourier-Domain Optical Coherence Tomography Imaging: Advantages and Future Development", Curr Cardiovasc Imaging Rep (2012) 5:221-230.

E. W. Dijkstra, "A note on two problems in connexion with graphs," Numerische Mathematik, vol. 1, No. 1, pp. 269-271, 1959.

Falcao, et al., "An Ultra-Fast User-Steered Image Segmentation Paradigm: Live Wire on the Fly", IEEE Transactions on Medical Imaging, vol. 19, No. 1, Jan. 2000.

Friedman, et al., "Bayesian Network Classifiers", Machine Learning, 29, 131-163 (1997).

Goldberg, et al., "A new Approach to the Maximum-Flow Problem", Journal of the ACM (JACM), vol. 35, No. 4, pp. 921-940, 1988.

Gurmeric, et al., "A New 3-D Automated Computational Method to Evaluate In-Stent Neointimal Hyperplasia in In-Vivo Intravascular Optical Coherence Tomography Pullbacks", Med. Image Comput. Comput. Assist. Interv., vol. 12, pp. 776-785, 2009.

Klein, et al., "Automatic segmentation of the wire frame of stent grafts from CT data", Med. Image. Anal., vol. 16, No. 1, pp. 127-139, 2012.

Li, et al., "Optimal Surface Segmentation in Volumetric Images—A Graph-Theoretic Approach", IEEE Trans Pattern Anal Mach Intell., Jan. 28, 2016.

T. K. Moon, "The expectation-maximization algorithm," IEEE Signal Process Mag., vol. 13, No. 6, pp. 47-60, 1996.

Okamura, et al., "3-Dimensional Optical Coherence Tomography Assessment of Jailed Side Branches by Bioresorbable Vascular Scaffolds a Proposal for Classification", J. Am. Coll. Cardiol. Intv., vol. 3, No. 8, pp. 836-844, Aug. 1, 2010.

J. C. Picard, "Maximal closure of a graph and applications to combinatorial problems," Management Science, pp. 1268-1272, 1976.

F. Rosenblatt, "The perceptron: A probabilistic model for information storage and organization in the brain," Psychol. Rev., vol. 65, No. 6, pp. 386, 1958.

Stone, et al., "Everolimus-eluting versus paclitaxel-eluting stents in coronary artery disease,". Engl. J. Med., vol. 362, No. 18, pp. 1663-1674, 2010.

Tearney, et al., "Evaluation of intracoronary stenting by intravascular optical coherence tomography", Heart, vol. 89, No. 3, pp. 317-320, Mar. 1, 2003.

Ughi, et al., "Automatic segmentation of in-vivo intra-coronary optical coherence tomography images to assess stent strut apposition and coverage," Int. J. Cardiovasc. Imaging., 2011.

Unal, et al., "Stent implant follow-up in intravascular optical coherence tomography images," Int. J. Cardiovasc. Imaging., vol. 26, No. 7, pp. 809-816, 2010.

Wang, et al., "Automatic stent strut detection in intravascular optical coherence tomographic pullback runs," Int. J. Cardiovasc. Imaging., vol. 29, No. 1, pp. 29-38, 2013.

Wang, et al., "Volumetric quantification of fibrous caps using intravascular optical coherence tomography," Biomed. Opt. Express., vol. 3, No. 6, pp. 1413-1426, 2012.

Xu, et al., "Automatic detection of stent struts with thick neointimal growth in intravascular optical coherence tomography image sequences," Phys. Med. Biol., vol. 56, No. 20, pp. 6665, 2011.

Wang, et al., "Automatic segmentation of intravascular optical coherence tomography images for facilitating quantitative diagnosis of atherosclerosis," Proc. SPIE, vol. 7889, pp. 78890N, 2011.

R.C. Prim, "Shortest Connection Networks and Some Generalizations", Bell Syst. Tech. J., vol. 36, No. 6, pp. 1389-1401, 1957.

* cited by examiner

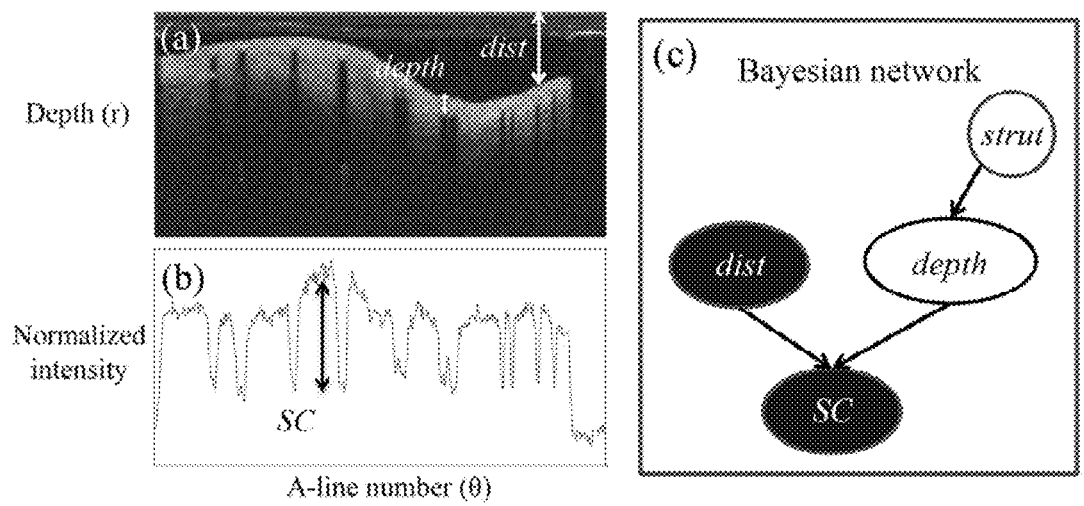
Figs. 4A-C
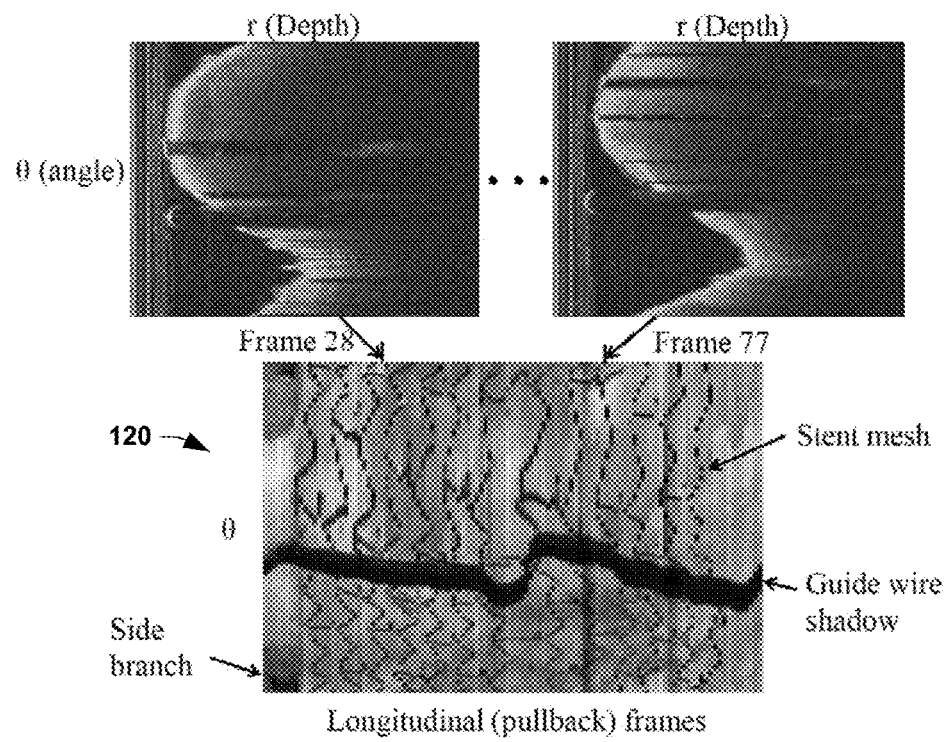
Fig. 5

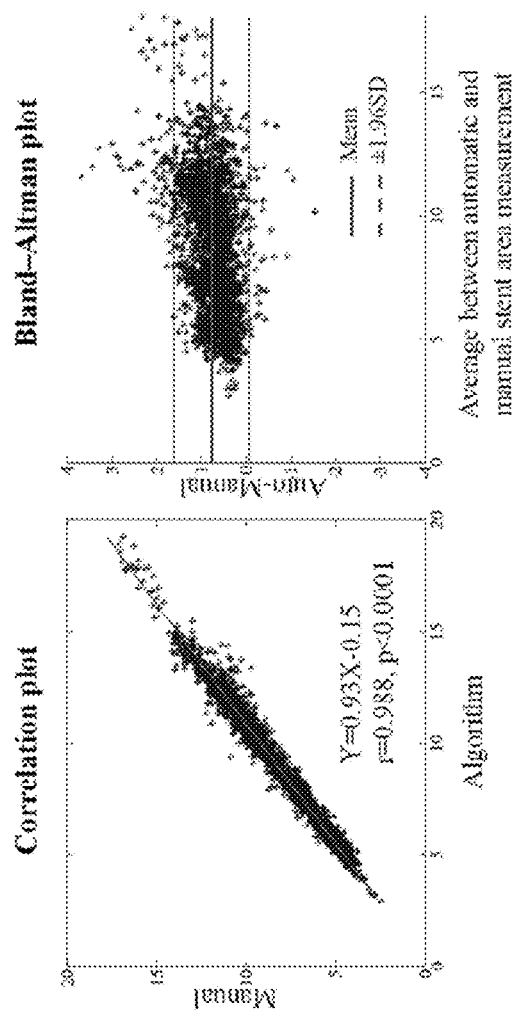
Fig. 11
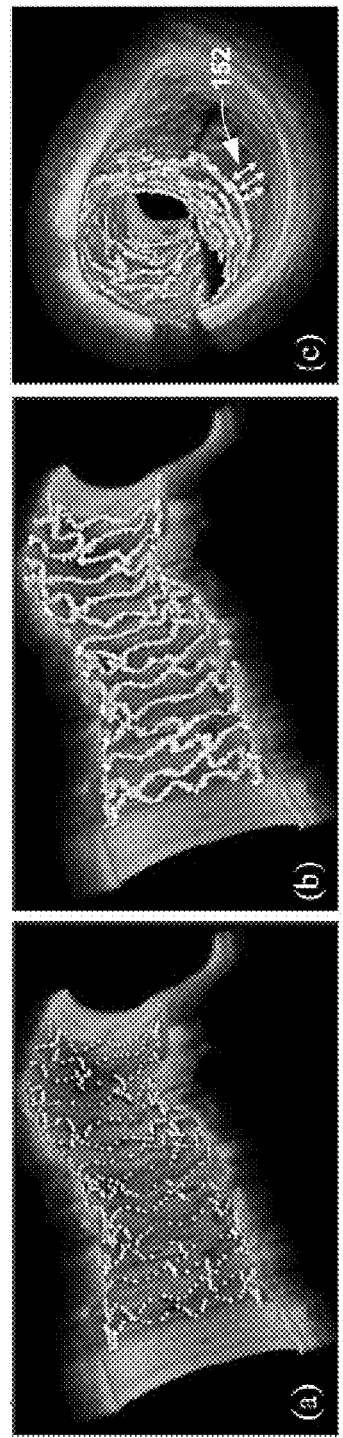
Figs. 12A-C

ANALYSIS OF OPTICAL TOMOGRAPHY (OCT) IMAGES

CROSS REFERENCE TO RELATED APPLICATION

This application claims the benefit of U.S. Provisional Patent Application No. 62/108,408, filed Jan. 27, 2015, and entitled ANALYSIS OF OPTICAL TOMOGRAPHY (OCT) IMAGES, which is incorporated herein by reference in its entirety.

GOVERNMENT FUNDING

This invention was made with government support under Grant Nos. R01HL114406 and R21HL108263 awarded by The National Institutes of Health. The United States government has certain rights to the invention.

TECHNICAL FIELD

This disclosure relates to systems and methods for analysis of optical coherence tomography (OCT) images, such as images of stents.

BACKGROUND

Stent implantation via percutaneous coronary intervention (PCI) is a popular coronary revascularization procedure for patients with atherosclerosis. Various stent types have been designed to improve the efficacy of stent treatment. Extensive preclinical and clinical studies are needed to evaluate these newly developed stent designs. For example, every year, hundreds of thousands of patients with coronary artery diseases in the U.S. are treated with intra-vascular stents. Improper deployment of stents and resulting tissue responses are associated with stent thrombosis, which can be a life-threatening complication. Intravascular optical coherence tomography (OCT) is a catheter-based optical imaging technique and is able to image the depth-resolved 3-D profile of coronary arteries with very high resolution (10-20 µm). OCT has demonstrated significant advantages in strut coverage analysis due to better resolution and contrast compared to the alternative technology, intravascular ultrasound (IVUS), which has a resolution about 100-200 µm.

BRIEF DESCRIPTION OF THE DRAWINGS

FIGS. 4a, 4b and 4c illustrate part of image analysis used to identify determine strut contrasts.

FIG. 5 illustrates examples of OCT image frames and a corresponding synthesized en face projection image.

FIG. 11 illustrates correlation plots of the stent area measurements based on stent strut detection by the automated algorithm and by human analysts.

FIGS. 12a, 12b and 12c illustrate example 3-D reconstructions of an implanted stent from an intracoronary OCT pullback.

DETAILED DESCRIPTION

Overview

Figure 1:
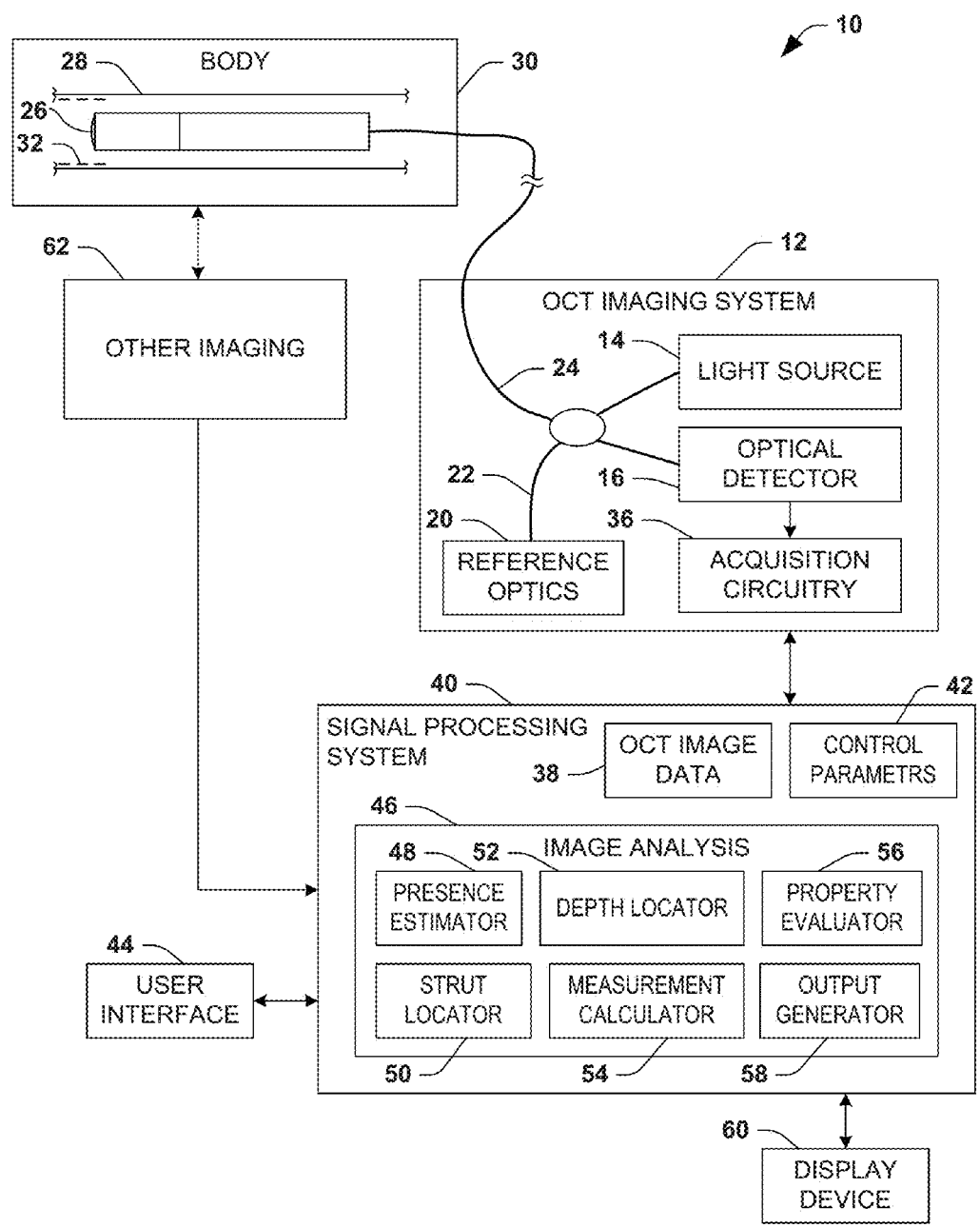
FIG. 1 is a block diagram illustrating an example of an optical coherence tomography system for analysis, visualization and characterization of intravascular stents.

This disclosure provides systems and methods for detection of stent structures in OCT images.

As an example, a Bayesian network can be implemented based upon physical principles of OCT imaging and a probability of stent strut appearance in an A-line can be computed. The stent wire continuity from adjacent frames can be exploited and a method based on minimum spanning trees and shortest path algorithms can be provided to detect the stent strut locations in an en face view. A graph cut algorithm further can be utilized to facilitate concurrent analysis of the physical stent model and localization of the depths of all the stent struts in a pullback. The approach disclosed herein can perform robustly with images encountered in the clinical environment.

Increased robustness can be realized through: (1) Using a Bayesian network based on image formation physics to lessen potential problems of overtraining. (2) Using machine learning from many manually analyzed cases and avoid as much as possible, case dependent parameters from hand crafted algorithms (3) Using high-level knowledge of stent cylindrical shape and stent wire continuity. (4) Incorporating graph search methods which allow one to use global information to detect and localize stent struts such as adjacent strut, adjacent frame and 3-D stent mesh information to facilitate robust stent strut detection.

By employing automated detection of stents, the approach disclosed herein may benefit at least three applications: 1) Offline analysis of large clinical trials; 2) Live-time feedback during stent deployment, and 3) Live-time information for potential support of treatment decisions. All of these applications can help improve patient care.

Systems and methods disclosed herein facilitate stent strut detection and analysis, which uses 3D information about stents. Briefly, the systems and methods can employ formation physics and machine learning via a Bayesian network, and 3-D knowledge of stent structure via graph search. Graph search was done on en face projections using minimum spanning tree algorithms. Depths of struts in a pullback were simultaneously determined using graph cut. Automated strut detection achieved a 0.91±0.04 recall, and 0.84±0.08 precision. Performance was robust in images of varying quality. This method can improve the workflow for analysis of stent clinical trial data, and can potentially be used in the clinic to facilitate real-time stent analysis and visualization, aiding stent implantation.

With superior resolution and imaging speed, intravascular OCT (IVOCT), according to the systems and methods disclosed herein, can also be utilized for in vivo assessment of vessel healing after stent implantation. For instance, the methods can be employed to compute a percentage of stent struts with tissue coverage. Percentage of covered stent struts is a potential biomarker for late stent thrombosis (LST). Percentage of covered struts assessed by IVOCT can be an important metric for evaluating stent viability. In addition to covered/uncovered, the systems and methods disclosed herein may be employed to measure tissue coverage thickness, stent area, lumen area, and tissue coverage area.

Description of Example Embodiments

FIG. 1 depicts an example of an optical coherence tomography system 10 for analysis, visualization and characterization of implanted objects, such as intravascular stents. The system 10 includes an OCT imaging system 12. The OCT imaging system 12 can be implemented according to a variety of different platforms, including time-domain optical coherence tomography (TD-OCT) or frequency-domain optical coherence tomography (FD-OCT). Some examples of FD-OCT include spectral domain OCT (also known as spatially encoded frequency domain OCT) and swept source OCT (also known as time encoded frequency domain OCT). These OCT systems use a reference arm and an interferometer to detect echo time delays of light. The interferometer uses a beam splitter, dividing the light into a measurement arm (tissue sample) and a reference arm. The reference arm in TD-OCT is mechanically scanned (e.g., by a moving mirror longitudinally in time) to produce a time-varying time delay. In the FD-OCT, because the light source is frequency swept, the interference of the two light beams (tissue and reference) oscillates according to the frequency difference. Additionally, in FD-OCT the broadband interference is acquired with spectrally separated detectors (e.g., by encoding the optical frequency in time with a spectrally scanning source or with a dispersive detector, like a grating and a linear detector array) and depth scan can be immediately calculated by Fourier transform from the acquired spectra in the image without moving the reference arm. Thus, since all echo delays are acquired simultaneously, significant increases in the speed of image acquisition can be realized, In both TD and FD types of OCT systems the interference of the signal ultimately provides amplitude and frequency data.

With reference to FIG. 1, regardless of the type of OCT platform, the OCT imaging system 12 includes a light source 14 and a detector 16 coupled to a beam splitter 18 via corresponding optical fibers or other waveguides. A reference arm 22 implements corresponding reference optics 20 that are coupled to the beam splitter via an optical fiber. A sample arm 24 employs a corresponding OCT probe 26 that is coupled to the beam splitter via an optical fiber to acquire optical signals. As an example, the probe 26 can be inserted into a patient's body 30, such as positioned within a vascular lumen 28, for acquiring OCT images of the inside of the lumen. Of particular interest, the acquired images can include an implanted object 32, such as a stent, positioned within the lumen 28.

As disclosed herein, the OCT imaging system 12 can acquire OCT images before, during and/or after deployment of the stent 32 within the vessel lumen 28. For instance, the OCT images can be analyzed and generate feedback during deployment of the stent 32, such as by inserting the probe concurrently with the catheter apparatus used for stent placement and deployment. In other examples, the probe 26 can be inserted within the lumen separately from the implantation process to acquire OCT images of the stent post implantation.

Various probe designs can be used to acquire the optical signals within the lumen 28. The probe 26 can include rotating optics or the probe itself can be rotatable about its longitudinal central axis for acquiring images as it rotates about its axis. The rotation can be automatic and controlled (e.g., in response to activation of a motor) or, in other examples, the rotation of the probe 26 about its longitudinal axis can be implemented manually. In addition to rotational motion of the probe 26 the probe itself can be moved at different speed along the axial direction within the lumen 28. Again, the advancement or pullback of the probe can be manually implemented, such as along a guide wire that has been placed within the lumen 28. As an example, the probe 26 can be pulled back axially at a pullback speed sufficient to acquire a series of images along the lumen inner wall, which is at least co-extensive with the axial position where the stent structure 32 resides.

As mentioned, the OCT imaging system 12 can be implemented as a time-domain OCT system, a spectrum-domain OCT system or a swept source OCT system. Thus the components of the OCT imagining system 12, including the light source 14, reference optics 20 and corresponding acquisition circuitry 36 are configured according to the type of OCT system being implemented. The acquisition circuitry 36 can include an arrangement of one or more amplifiers and an analog digital converter for providing OCT image data 38 that can be sampled over a period of time (e.g., in response to a sample clock—not shown) and stored in memory (e.g., a non-transitory machine readable medium).

The OCT image data 38 is processed by a corresponding signal processing system 40. The signal processing system 40 can also implement controls associated with the OCT imaging system 12 such as controlling location and/or movement of the probe 26 within the lumen 28. For example, the controls can set one or more control parameters 42 for controlling various parameters of the OCT imaging system 12, such as including parameters of the light source 14 (e.g., wavelength, power, etc.) and/or the detector 16 (e.g., detection acquisition rate used for acquiring for the OCT imaging 38). The control parameters 42 and resulting images can be further controlled in response to the user input via a user interface 44. For example, the user interface 44 can synchronize the image capture process with deployment of the stent or otherwise trigger OCT image acquisition in response to a user input during movement of the probe 26.

The signal processing system 40 also includes image analysis 46. The image analysis method 46 is programmed to analyze the OCT image data 38 acquired via the OCT imaging system 12. For example the OCT image data 38 corresponds to a plurality of sequential image frames acquired by the OCT imaging system 12 as the probe 26 within the lumen 28 is moved in a predetermined manner. For example, the probe 26 can be advanced axially to a desired position beyond the distal axial end of the stent 32 and then pulled back axially at a controlled speed. The OCT image data 38 thus can include an OCT image set of a plurality of frames corresponding to the pull back of the probe 26 axially within the lumen 28 from a point axially beyond the distal end stent 32 to an axial position that passes by the opposite axial end of the stent. The OCT image data 38 can include a single pullback event or it can encompass multiple pullback events with different operating parameters for the OCT imaging system.

The image analysis 46 can include a presence estimator 48 to analyze the image data 38 and compute a probability estimate of stent presence at support positions appearing in an A-line with respect to the probe 26. As a further example, the presence estimator 48 can generate a corresponding two-dimensional en face image based on the image data 38. A strut locator 50 of the image analysis 46 can further segment the en face image to determine the corresponding strut locations. Segmentation thus can identify strut locations from the OCT image data from the en face image that is generated from the OCT image data generated during pullback, for example. The strut locations from the en face image can be utilized to reinforce computed probability estimate of stent presence from the OCT image data 38 over a plurality of frames that form the corresponding image set for a length of the lumen that includes the stent 32. As a further example, the reinforcement of the probability estimate of strut presence can implement a minimum spanning tree method, such as disclosed herein. The strut locator 50 thus can identify strut locations in a three dimensional image space based on the probability estimate computed by the presence estimator 48 for the acquired sequence of images in the image data 38.

The image analysis 48 can also include a depth calculator 52 to determine strut depth along the A-line or other locations. As a further example, the depth calculator 52 can identify high confidence struts based upon initial estimate of strut depths. A refined estimate of strut depth for such high confidence strut can then be determined. Strut depths at other locations can then be interpolated based on the refined estimate of strut depths for the high confidence struts to provide corresponding interpolated strut depths for a set of other locations. A final probability estimate of strut presence can then be determined based on the interpolated strut depths and the high confidence struts that have been identified. In some examples, the depth calculator 52 can use a graph cut method to localize depths of stent struts based on the OCT image data 38. For example, the graph cut method implemented by depth calculator 52 can concurrently localize the depths of struts based upon the image data 38 that is acquired during pullback, for example. Additionally, it is understood that while the image analysis 46 can be utilized from image data acquired at any axial position within the lumen 28, the corresponding image data 38 further can correspond to images acquired during one or more OCT pullbacks in which the probe 26 is axially pulled back within the lumen 28 so that the acquired images include the entire axial length of the stent structure 32.

The image analysis 46 can also include a measurement calculator 54 to compute one or more measurements based upon the identified strut locations. The measurements at the strut locations that have been identified can include computing stent area, a malapposition area of the stent and/or a neointima area of the stent. The measurement calculator 54 can also compute a coverage thickness for one or more of the struts. In other examples, a malapposition distance can be computed for a pair of struts by the measurement calculator 54, such as if the malapposition distance between struts exceeds a predetermined distance (e.g., fixed or user programmable distance).

The corresponding measurements can be stored in memory, such as associated with the image data corresponding to metadata describing the measurements and other information determined from the OCT image data 38. For instance, image data and 3D locations where such measurements have been made can be tagged or otherwise linked to the respective measurements. In this way, subsequent analysis of the image data can provide an indication of the measurements that have been computed by the measurement calculator 54 for respective locations where such information. User annotations can also be added via the user interface to the image data (e.g., as metadata).

Image analysis 46 can also include a property evaluator 56 to evaluate properties of the stent 32 and/or the vessel 28.

As mentioned, for example the stent 32 can be implemented as a metallic stent or a bio-absorbable stent (e.g., having no metal). The property evaluator 56 thus can be utilized to analyze the OCT image data 38 to determine properties of the metallic stent. The evaluation of properties can include information acquired solely from the OCT image data that is acquired for the implanted stent 32 or the property evaluator 56 can form a comparative analysis relating to known properties of other stents with different designs. The comparison with other stents can be utilized to determine the efficacy of the stent 32 relative to other possible designs or implantations. Similarly, for the example of a bio-absorbable stent, the property evaluator 56 can analyze the image data 38 to determine properties of the bio-absorbable stent including properties of the stent itself or comparative analysis of the stent 32 relative to properties of stents with similar platforms or structures.

The signal processing system 40 can also include an output generator to generate a graphical output that can be presented via a display device 60. The output generator 58 can provide images in real-time during the procedure in which the probe 26 is moved within the lumen 28. In other examples, the output generator 58 can perform image processing on a plurality of image frames that have been acquired and stored as the image data 38 that have been process to identify strut locations and, in turn, visualize a three-dimensional graphical representation of the stent structure 32 and the lumen 28. The particular type of image, such as a real-time image acquired by the OCT imaging system 12 or a composite image generated by the output generator 58 from a plurality of frames acquired during pull back of the OCT probe, can be determined based upon a user input entered via the user interface 44. In some examples, as disclosed herein, the output generator 58 can superimpose the identified strut locations that have been determined to provide a graphical representation of such struts with respect to image data acquired by one or more image modalities (e.g., fluoroscopy, intravascular ultrasound or the like). For instance the OCT image can be co-registered with the image acquired by the other imaging modality to provide a composite image. The OCT imaging thus provides a high resolution 3-D image of the stent and the interior of the lumen 28, which resolution exceeds that available from the other imaging modality.

By utilizing the OCT imaging system intraprocedurally, real-time feedback can also be provided during the positioning and, ultimately, deployment of the stent 32. The images displayed on the display device 60 thus can provide visual feedback to enable a user to implement corrective action to mitigate malapposition, such as re-deployment (e.g., via balloon catheter) or other position adjustments to ensure proper contact between the stent struts 32 and the lumen wall 28. Additionally or alternatively, images displayed on the display device 60 thus can provide visual feedback post-implantation of the stent 32. For instance, post implantation, the OCT imaging system can acquire OCT images of an employment stent to provide feedback and associated quantitative metrics, such as stent area strut coverage in an automated manner, which can be used to identify neointima that forms which may require corrective action (e.g., excision).

Figure 2:
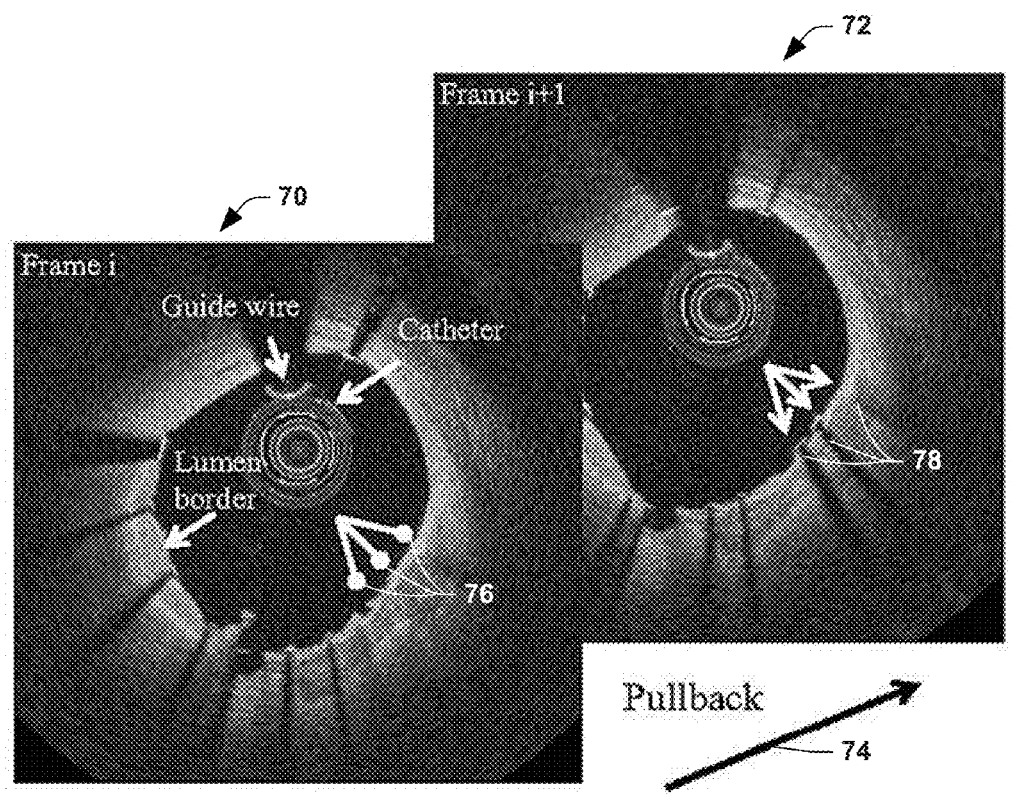
FIG. 2 depicts images illustrating examples of adjacent frames from an OCT pullback showing stent struts.

FIG. 2 depicts an example of adjacent frames (Frame i and Frame i+1) that can be obtained and generated by the output generator 58 during pull back in a direction demonstrated at 74. In each of the image frames 70 and 72, the lumen border is shown as well as a guide wire along which the probe and catheter can be advanced within the lumen.

The stent struts in each of the image frames 70 and 72 are demonstrated as bright reflections followed by dark shadows. For example, in image frame 70 oval arrows at 76 demonstrate potentially ambiguous struts. From further analysis from image frame 72 it is clear that the ambiguous structure in frame i correspond to leading edges of clearly identified struts 78 also demonstrated by arrows. Thus, the image analysis 46 of FIG. 1 can be used to identify and reinforce strut locations that may be potentially ambiguous in different frames.

Figure 3:
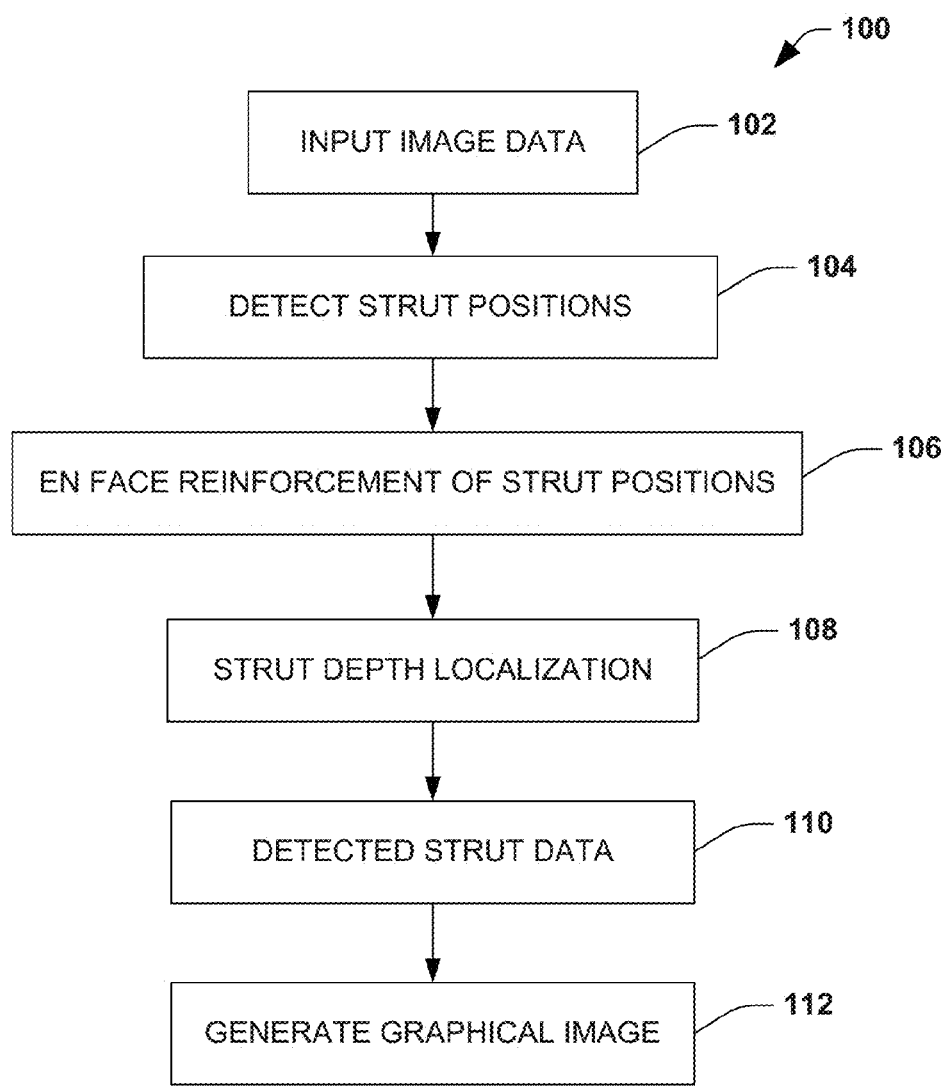
FIG. 3 is a flow diagram illustrating an example of an automated stent detection method.

FIG. 3 demonstrates an example method 100 that can be employed to analyze OCT image data (e.g., image data 38) to detect stent struts. The method 100 can be implemented as machine-readable instructions executed by a processor, such as corresponding to the image analysis method 46 disclosed herein. Thus, additional context of the system and image data acquisition and image analysis method that can be utilized can be had with reference back to the system of FIG. 1. The method begins at 102 as OCT image data is input (e.g., from an OCT imaging system 12). The input image data can be acquired at 102 by any one or more configurations of OCT platform disclosed herein (e.g., time-domain OCT system, a spectrum-domain OCT system or a swept source OCT system). The image data input at 102 can be real time image data acquired and processed intraprocedurally or the acquired data can be stored and accessed following a procedure.

Figure 7:
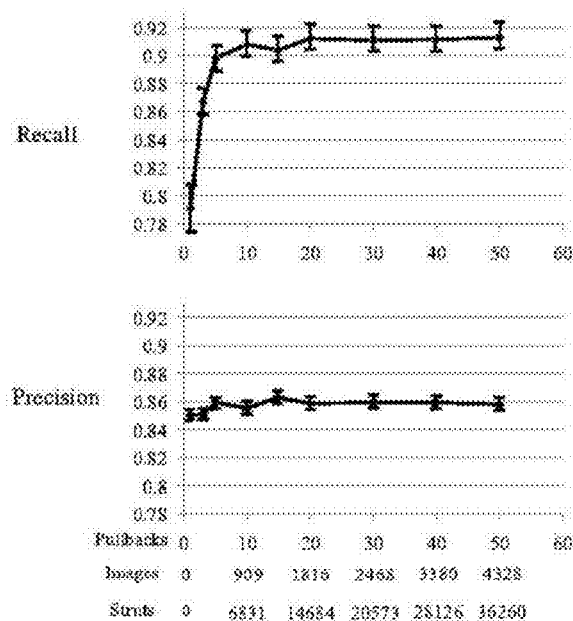
FIG. 7 depicts graphs demonstrating the effect of the size of the training data set on the performance of Bayesian classification for recall and precision.

At 104 strut positions are detected (e.g., by presence estimator 48 and/or strut locator 50). For example, the strut positions can be detected by implementing a Bayesian approach to estimate the presence of possible strut positions from the acquired image data. FIG. 7 illustrates the effect of the size of the training data set on the performance of Bayesian classification. In the example of FIG. 7, the testing data are a subset of randomly selected 10 pullbacks from the entire validation data set.

At 106, the method includes en face reinforcing of the strut positions detected at 104. For example, the stent positions can be reinforced using 3-D stent mesh information in an en face projection view. At 108, the method includes implementing strut depth localization. For example, the depth locations of all struts in a pullback are simultaneously determined (e.g., by strut depth locator 52), such as by using spatial constraints between adjacent struts to maintain a tubular structure. Additional design details for a given stent configuration, such as model and manufacturer, can be known a priori and used to impose geometrical constraints among adjacent struts.

At 110, detected strut data is provided. The detected strut data can be stored in memory to describe stent strut geometry in three-dimensional space, such as registered to patient geometry (e.g., within a vessel) or in image space associated with the OCT imaging system, for example. At 112, a graphical image of the stent can be generated based on the detected strut data. The image can be a two-dimensional or three-dimensional image rendered in a display device (e.g., display device 60). In some examples, the visualization can be manipulated in response to a user input to vary the perspective and/or viewing angle of the stent and/or lumen in which the stent is positioned.

In the following sections, additional example information about implementing each part of the method 100 of FIG. 3 is disclosed.

A. Image Preprocessing (e.g., by Signal Processing System 40)

The systems and methods employ an OCT system (e.g., system 12) to acquire OCT image data. As one example, OCT images may be acquired by commercial Fourier Domain OCT systems (C7-XRTM OCT Intravascular Imaging System, St. Jude Medical Inc., St. Paul, Minn.). In this example OCT system, the axial resolution of the OCT system may be about 15 μm. The scan characteristics of the system are: 50,000 lines/s, 504 lines/frame, yielding 100 fps and 20 mm/s pullback speed yielding a 200 μm frame interval. Other systems with different resolutions and/or scan characteristics can be utilized.

As part of the image preprocessing (e.g., by signal processing system 40), the OCT raw data can be logarithmically compressed and operated upon in polar coordinate (θ, r). For instance, calibration can be performed by adjusting the z-offset according to a priori knowledge of the catheter size. The luminal boundary of the vessel, and guide wire artifacts can be robustly identified using a dynamic programming algorithm, such as are known. The luminal boundary information is used in subsequent stent detection.

B. Detection of Strut Positions

As disclosed herein, strut positions can be estimated (e.g., by presence estimator 48) using a Bayesian network. As an example, the first stage is to detect A-lines in angle θ containing stent struts. As metallic stent struts strongly reflect light, each strut casts a dark shadow in the (θ, r) image (see FIG. 4). FIG. 4a illustrates an example an original OCT image in polar coordinates. FIG. 4b illustrates an example of normalized intensity along the A-line. For example, the mean intensity of the A-line can be computed (e.g., by measurement calculator 54) within a fixed depth from the lumen boundary, and the resulting 2-D image projected into a 1-D curve of normalized intensity along the A-line. Struts will generate local minima and have large strut contrasts, SC. The 2-D polar coordinate image of FIG. 4a (from preprocessing) can be projected into one dimension (FIG. 4(b)) by averaging intensity values along each A-line between the lumen and a depth of approximately 1.5 mm, the nominal imaging depth in OCT. Local minima in this curve can be computed to correspond to strut locations. The determined strut locations can be stored in memory.

The physical principles may further be considered in the detection of struts in the 1-D projection curve. For example, only some local minima are caused by struts. Others are from artifacts or tissue intensity differences between adjacent A-lines. The relative difference between adjacent peak and valley points can be defined to be shadow contrast (SC). Based upon physics and observation, it can be determined that the magnitude of SC depends on the distance from the catheter to the lumen wall (represented by dist) and by the thickness of the tissue covering the strut (represented by depth). When the lumen boundary is far from the catheter (high dist), signal intensity drops as the beam is out of focus. For deeply embedded struts (high depth), there is more signal accumulated from tissue superficial to the strut. In both cases, SC will be smaller.

These cause-effect relationships can be modeled using a Bayesian network such as shown in FIG. 4(c). FIG. 4c demonstrates a Bayesian network representation based on principles of OCT image formation. Known variables are marked as dark nodes in FIG. 4c. The Bayesian network depicted in FIG. 4(c) encodes the causal dependencies between variables and compactly represents the full joint probability distribution defined by all the variables. For example, in FIG. 4(c), the arrows link the causes (also parents) dist and depth to the effect (also child) SC, and this is consistent with the discussions above. The node SC also encodes the conditional probability P(SC|dist,depth), i.e., probability of SC being a certain value given the observed values of dist and depth. For baseline cases where the OCT is performed immediately after stent implantation, there will be no tissue covering the struts. Accordingly, in such examples, the network can be simplified by not considering the strut depth.

Formally, a Bayesian network is a directed acyclic graph (DAG) in which each node X has a conditional probability distribution P(X|Parents(X)) that quantifies the effect of the parents on the node. An important feature of a Bayesian network is that each variable is independent of its nondescendants given its parents. Given some observed variables and known conditional probabilities, the posterior probabilities of the unknown variables can be computed using probability theory.

In the stent detection problem demonstrated in FIG. 4, the probability of strut presence can be queried among all the peaks given our observations. Here, the values of SC and dist can be directly observed from the OCT images. The probability of strut presence, P(strut), and P(SC|dist,depth) can be estimated from manually analyzed training data, for example. As SC, dist and depth are continuous variables, they can be discretized into bins to generate the conditional probability tables (e.g., for depth an additional value undefined can also be included to make it compatible with presence of no strut). Note that the strut depth is a latent variable because struts are not yet detected. According to probability theory, the probability of strut presence P(strut|SC,dist) given values of SC and dist can be directly queried, by marginally summing over all the possible depths a strut could occupy, such as follows:

$$P(strut \mid SC, dist) = \frac{\sum_{depth} P(SC, dist, depth, strut)}{\sum_{strut} \sum_{depth} P(SC, dist, depth, strut)} \quad (1)$$

where strut is a binary variable present or not present.

However, in some cases, such an approach may be noisy for strut not-present and ambiguous strut positions where the strut depth is either undefined or ambiguous. On the other hand, the strut depth is well-defined in high confidence strut A-lines with a reflection-shadow appearance. Since adjacent struts are likely to be imbedded at similar depths below the tissue (FIGS. 2 and 4), high confidence strut depths can be used to estimate the depths in surrounding locations. Based on these considerations, the method disclosed herein can be utilized, in some examples, to compute a quick estimate of strut depth and then improve estimates of the probability of strut presence and strut depth in subsequent processing.

Estimate-Strut-Presence

As disclosed herein, strut presence can be detected in a multi-part detection process (e.g., by presence estimator 48) that includes an initial location estimation (at 104) and then reinforcement of strut positions (at 106). The following algorithm provides an example of a method that can be utilized to detect stent presence based on OCT image data.

By way of example, the approach can include computing a rough estimate for the strut depth bin for each of the peaks in the 1-D projection (i.e., suspected struts) using maximum likelihood estimation (MLE):

$$depth_{MLE} = \underset{depth}{\mathrm{argmax}} P(SC \mid dist, depth) \quad (2)$$

Next, high confidence struts can be identified by estimating P(strut|SC,dist) and selecting only the peaks that are associated with high probability (e.g., 0.7) of strut presence. Notice that strut depth can be treated as a deterministic variable by using the estimated depth bin from the proceeding rough estimate (e.g., from Eq. 2). From this estimate, equation (1) can now be evaluated using the equations below.

$$P(strut \mid SC, dist) = \frac{P(SC, dist, depth_{MLE}, strut)}{\sum_{strut} P(SC, dist, depth_{MLE}, strut)} = \quad (3)$$

$$\frac{P(SC \mid dist, depth_{MLE})P(dist)P(depth_{MLE} \mid strut)P(strut)}{\sum_{strut} P(SC \mid dist, depth_{MLE})P(dist)P(depth_{MLE} \mid strut)P(strut)} =$$

$$\frac{P(SC \mid dist, depth_{MLE})P(depth_{MLE} \mid strut)P(strut)}{\sum_{strut} P(SC \mid dist, depth_{MLE})P(depth_{MLE} \mid strut)P(strut)}$$

Additionally, strut depths of high-confidence struts identified in Step 2 can be determined, and these high-confidence depth locations can be further used to interpolate strut depths for other suspected struts in the 1-D projection curve. The refined strut depth can be determined by searching the A-line within the depth bin found in Step 1 for the point r* that optimizes an objective function associated with strut features. For a given point r a linear objective function that models the strut presence can be used by combining the features of bright strut reflection, low intensity shadow and high gradient at the strut-shadow transition $$f_r = S_r + \mu I_r + \lambda M_r \quad (4)$$

where:
Sr is the slope of the A-line segment Lr following r to greater depths in the tissue;
Lr is selected to be 70 μm long to cover the transition between the bloom and the shadow;
Ir is the intensity at r;
Mr is the mean intensity of the A-line segment (500 μm long) after Lr, representing the intensity of the shadow; and
Variables μ and λ are weights, such as can be determined using methods described herein below.

Interpolation uses the same method as used for stent area quantification disclosed herein. For those images where there are no high-confidence struts, the computations using high-confidence strut data (Eq. 4) can be omitted from the method, and the result from Eq. 3 can be utilized directly.

Following calculating Eq. 4 (or Eq. 3 wherein no high-confidence struts exist), the final estimated probability P(strut|SC,dist) can be determined using (3) with the updated depth information found in Step 3 for all suspected struts.

In summary, for a given new local minimum from the 1-D A-line projections, SC and dist can be obtained directly and depth from Eq. 2 can be estimated based on pre-learned probabilities P(SC|dist,depth) from training data. The estimate of strut depth above can be computed by combining information from within the A-line and from adjacent struts. Finally, the final probability of strut presence in the A-line can be determined using Eq. 3 and the updated depth. This is similar to the expectation-maximization algorithm but with incorporation of the application-specific knowledge relating to high-confidence struts. For baseline cases (i.e., no tissue coverage), P(strut|SC,dist) can be directly estimated without considering the strut depth. Thus at the end of this stage of the estimate strut presence algorithm, the method can identify all A-lines in the pullback that apparently contain stent struts. Furthermore, a probability is associated with each identified strut location (e.g., stored in memory with each identified strut), so that high-confidence struts can be specified by simply thresholding the probability values.

C. En Face Reinforcement of Strut Locations

In this stage of the algorithm, stent wire continuity is used to reinforce possible stent strut positions obtained from the probabilistic network in the first stage, and to capture some ambiguous struts (see, e.g., struts 76 of FIG. 2) that would be missed using only single frame processing. The approach disclosed herein uses all the 1-D projections computed as above, over a plurality of the frames (e.g., all the frames) in the stented region of the pullback. The result is a 2-D en face projection image showing the structure of the stent image demonstrated at 120 in FIG. 5. In FIG. 5, the en face projection is displayed as a function of distance along the pullback (along the vessel longitudinal axis) and θ around the probe. Also shown in FIG. 5 are examples of a plurality of OCT image frames (e.g., frames 28 and 77) in polar coordinates from the stented portion of a pullback. As a result of the acquired OCT image frames, the en face projection image 120 can be generated, giving an image as though the vessel was cut open longitudinally, flattened, and projected to the viewer. It is clear from the en face projection image 120 in FIG. 5 that the global structure of the stent mesh is well preserved showing well-organized and repeated units. The stent mesh in this view thus is segmented to reinforce the strut locations. This approach incorporates 3-D information of stent mesh structure, and it utilizes such information efficiently, i.e., instead of processing the whole 3-D image stack, the systems and methods disclosed herein only need to process a single en face projection image to determine strut locations in the entire pullback. As a result, the en face reinforcement part of the image processing facilitates real time analysis.

A potential problem with this approach is that, although the number of most commonly used stent types in US clinics is limited, there are actually more than 100 different stent designs in the current global market. There will certainly be more in the future. The resulting appearance of stent mesh in the en face projection view may have a plethora of possible patterns depending on the stent design. Therefore, a stent segmentation method may not generalize well if it makes too strong of an assumption about the mesh shape of a particular type of stent. Accordingly, the systems and methods may employ a "model-free" method that works well regardless of what type of stent is implanted, such as based on the minimum spanning tree (MST) technique from graph theory.

By way of example, consider an undirected graph G=(V, E) with vertices (nodes) V and edges E. A graph can be constructed with each vertex consisting of a pixel in the en face projection image, and with each edge defined by a connection between two pixels, as obtained in an 8-neighbour system. With edge weights equal to the average intensity of the two pixels in the en face projection image, a connected subgraph with low total edge weights will tend to trace out the dark stent wires. In graph theory, MST defines a subgraph that connects every vertex with a total weight minimizing all possible spanning trees. Suppose that there exist some seed points along the stent mesh, and it is desirable to connect them, a MST can generate a unique path between seed points and this path is very likely to follow the stent mesh where intensity is low. From the probabilistic output determined according to the probabilistic detection of strut positions using a Bayesian network disclosed above, seed points can be generated by applying a high confidence threshold (e.g., P>0.7). Hence, using MST, the paths linking seed points can be recorded, and all the paths to get the stent mesh can be combined.

However, MST alone may not generate a complete stent mesh because the stent mesh can have cycles, which is not possible with MST. Therefore, an additional 'rescue' procedure can be implemented to convert the resulting stent into a complete mesh. For instance, if two leaf nodes (i.e., nodes with no children) of the MST are "circumferentially" adjacent and connected in another non-shortest path, such nodes can be connected using Dijkstra's shortest path algorithm in which the low intensity stent mesh is again very likely to be covered. In some examples, a reasonable heuristic may be used to select the circumferentially adjacent region for two leaf nodes is to check whether they are within a 35-degree (circumferentially) by 3-frame (longitudinally) rectangular region.

As a further example, S may be defined as the set of seed points, edge weight $w(u,v)$ as the average intensity of u and v, $\Pi[v]$ as the parent of v in the tree, $key[v]$ as the minimum weight of any edge connecting v to a vertex in the tree, Q as a min-priority queue to store the unvisited vertices, r as any seed point chosen to be the starting point, P to store the path, $L[s]$ can be found to indicate whether the seed point is a leaf ($L[s]=1$). Prim's MST algorithm may be modified to provide a method for en face stent mesh detection, such as the following example MST-STENT algorithm (e.g., implemented by image analysis 46):

```
1    Initialize: Π[v] ← 0 , key[v] ← ∞ : ∀v ∈ V , Q ← V (G) ,
     P ← empty, L[s] ← 1 : ∀s ∈ S , key[r] ← 0
2    while Q is not empty
3        Extract u from Q
4        for each v adjacent to u
5            if w(u, v) < key[v] , Π[v] ← u , key[v] ← w(u, v)
6            if v ∈ S
7                Back track v until reach another seed point
                     s ' , add the path in P
8                L[s '] ← 0
9    for all the leaves found in MST
10       if there is no path in P within the circumferentially
             adjacent region between two leaf nodes
11           Link them using Dijkstra's shortest path
                 algorithm and add the path in P
12   return P
```

In line 7, s' always exists because Prim's algorithm maintains a single tree. The starting place can be one of the seed points, the root. In the worst case, s' will be the root. When the major loop (lines 2-8) is completed, there will be a MST and an intermediate stent mesh stored in P connecting all of the seed points. The loop 9-11 implements the rescue operation whereby the missing wires are filled in the stent mesh.

In practice, the intermediate stent mesh path might have traversed artifactual regions where the cost just happens to be low. Most commonly in practice, problems arise at vessel side branches (FIG. 5), which tend to be dark, bulky regions in the en face projection image. Side branches can be excluded before running MST-STENT using the following simple method. The en face projection image can be thresholded with a cut-off value given from the mean intensity of regions occupied by the seed point. A region is identified as a side branch if its area is larger than a pre-defined threshold (e.g., about 20 pixels). Another common artifactual region is the guide wire-blocked region (FIG. 4). However, this is segmented during preprocessing and can be excluded from the stent mesh.

En face stent mesh detection provides a high-level tool to augment the output of the probabilistic stage of the strut detection method. Specifically, an initial screening of stent locations is performed by including all candidate strut locations with at least a low confidence probability (P>0.3). A determination can be made to ascertain whether these struts are part of the stent mesh found in MST-STENT. If so, the struts can be retained; otherwise, they can be dropped. Combing this extra 3-D information for stent detection is potentially more robust than single frame processing.

Another benefit of en face stent mesh detection is for 3-D visualization. As the entire stent mesh can be detected, en face processing can potentially generate better 3-D visualization than using only the sparse stent struts detected in single frames. For the purpose of visualization, all the detected strut positions can be kept on the stent mesh in the en face projection view.

D. Simultaneous Depth Localization of all Struts

So far, the method has identified A-lines containing stent struts. The next step is to determine the precise depth location of the struts in those A-lines. A key feature presented here is that the depths of all struts can be localized simultaneously using a graph-search technique, whereas previous methods seem to detect depths one-by-one. Therefore, 3-D spatial information, including struts from neighboring frames, affords benefits not available on other approaches. Consider that a stent is a tubular structure, which is expanded at implantation. Unless there is a rupture, a very rare event, the implanted stent will maintain its tubular shape with some deformations caused by resistance from the vessel. Choosing the centroid of the lumen as the reference point, distances to struts are not likely to vary dramatically between adjacent struts. This enforces an important hard constraint on deformation that can be represented as follows:

$$|d_j - d_{adj(j)}| < T \quad (5)$$

where dj is the distance between a strut j to the lumen centroid, and adj(j) is the set of adjacent struts to strut j in 3-D space, and T is the deformation constraint.

In Eq. 5, 3-D adjacent struts include the ones in the same frame and across neighboring frames. Moreover, as OCT is scanned during a pullback in a helical pattern around the longitudinal probe axis, the last A-line of the current frame is also adjacent to the first A-line in the next frame. If a graph is constructed with each node formed by a pixel in the A-lines containing struts (termed strut line), and each node is associated with the objective function $f_r$ given in Eq. 4, the globally optimized depths for all struts corresponds to an optimal surface under the hard deformation constraint in the 3-D OCT pullback (see, e.g., FIG. 6).

Figure 6:
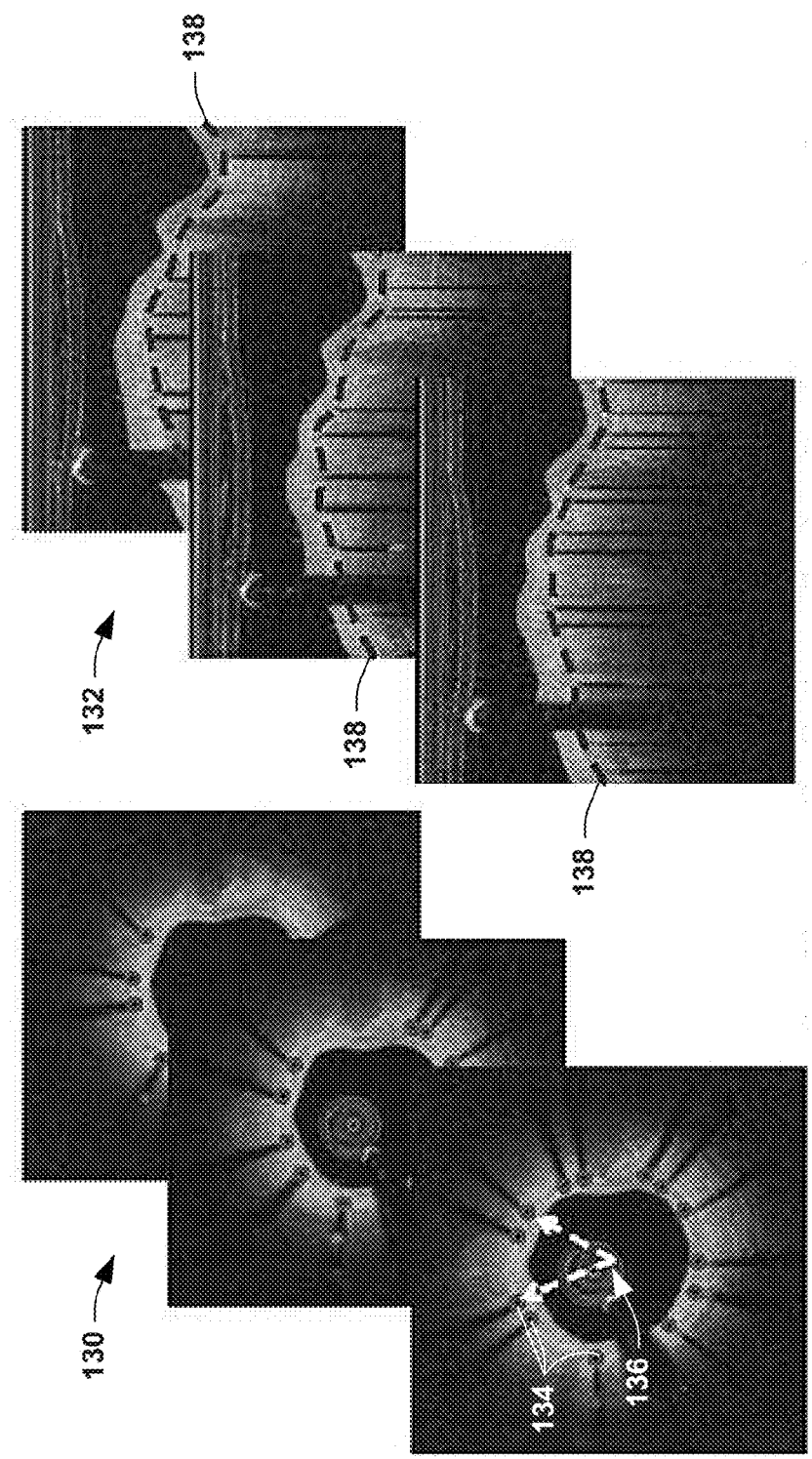
FIG. 6 illustrates an example of OCT image frames demonstrating transforming a strut depth determination into a graph search problem.

For example, FIG. 6 illustrates transforming the all-strut depth determination into a graph search problem. FIG. 6 includes representative image frames from an OCT pullback showing a stent implanted in a coronary artery with new tissue growth, displayed in Cartesian at 130 and in polar coordinates at 132. In the image frames 130, to maintain the tubular structure, the distances from adjacent struts 134 to the lumen centroid 136 are kept within a certain constraint in each frame. With the deformation constraint, the optimal depths (demonstrated as dashed line 138 in the different frames) for all the struts form the globally optimal surface in the graph constructed using only the pixels in the strut lines.

The optimal surface can be efficiently found using a specially constructed graph. The basic idea of the method is to transform the optimal surface search problem into an equivalent minimum closure search problem (where closure indicates that successors of any node are still in the set), which can be solved using graph cut algorithms.

As an example, the problem can be converted into a minimum closure problem with the following operations: 1) In each A-line containing a strut, the cost of each given node can be changed as the difference between the given node and the node immediately below. Here the lower nodes are the pixels farther away from the lumen. 2) For each node, make an edge to the node immediately lower than the current node; further, make an edge to the farthest lower node in 3-D adjacent strut lines it could reach under the deformation constraint. These edges are assigned infinite weights and are used as "shape priors" or "hard constraints." In particular, the intra-strut-line edges will ensure that a feasible surface will intersect each A-line exactly once. The inter-strut line edges ensure that distances of adjacent struts to the lumen centroid should not differ more than T. 3) Make the lowest layer nodes strongly connected (every node is reachable from other nodes). Under these conditions, the optimal surface corresponds to the optimal closure in the graph.

The optimal closure problem can be solved using graph cut algorithms according to Picard (see J. C. Picard, "Maximal closure of a graph and applications to combinatorial problems," Management Science, pp. 1268-1272, 1976.). Searching for the minimum cut is well studied and there are several efficient algorithms available. For example, the maximum flow algorithm developed by Boykov and Kolmogorov can be used (Y. Boykov, and V. Kolmogorov, "An experimental comparison of min-cut/max-flow algorithms for energy minimization in vision," IEEE Trans. Pattern Anal. Mach. Intell., vol. 26, no. 9, pp. 1124-1137, 2004.), although other algorithms may also be utilized.

E. Quantification of Clinically Relevant Metrics

After identifying stent strut locations in 3D space, various clinically relevant measurements can be made (e.g., by measurement calculator 54). Examples of such measurements include stent area (the area enclosed by the stent struts in a 2D image), malapposition area (area in a 2-D image enclosed by the lumen boundary and malapposed struts), neointima area (the area enclosed by the lumen boundary and the stent struts in follow-up cases where there is tissue coverage), and strut-level measurements (individual strut coverage thickness, malapposition distance, etc.). Additional other quantitative metrics that can be derived from the image and utilized herein, such as disclosed in Tearney et al. (G. J. Tearney, E. Regar, T. Akasaka et al., "Consensus standards for acquisition, measurement, and reporting of intravascular optical coherence tomography studies: a report from the international working group for intravascular optical coherence tomography standardization and validation," J. Am. Coll. Cardiol., vol. 59, no. 12, pp. 1058-1072, Mar. 20, 2012).

Once all the stent struts and the luminal boundary of the vessel are detected, any quantitative metrics, including but not limited to those mentioned above, can be computed. Specifically, all area measurements rely on obtaining a virtual stent contour from detected struts. As one example, a two-step interpolation scheme can be implemented to determine the stent contour. In this example, from detected stent struts, evenly-spaced virtual, "interpolated" points can be generated as to reside on a continuous surface extending between adjacent detected struts. These virtual points are placed at a depth from the luminal boundary which is linearly interpolated in the (r, θ) view from depths of adjoining struts. This process fills gaps between sparse struts. If the number of struts in the current frame is too small (e.g., less than a predetermined threshold), there will likely be large interpolation errors. In such cases, strut locations from adjacent ±1 frames can be combined for interpolation. Next, the complete stent contour can be generated from both real and virtual stent struts using cubic spline interpolation with respect to the catheter center. Although the foregoing describes the situation at follow-up where there are mostly covered struts, the above process also works for those instances where there are malapposed struts (and therefore negative depths).

Experimental Methods

A. Validation Data

The image sets used for the validation studies were collected from the database of the Cardiovascular Imaging Core Laboratory, University Hospitals Case Medical Center (Cleveland, Ohio). These images were collected by commercial Fourier-domain OCT systems (C7XR, St. Jude Medical Inc., St. Paul, Minn.), and have been previously analyzed by multiple expert analysts using commercial OCT workstations (St. Jude Medical Inc.) for other purposes. Example statistics describing the validation data are listed in Table 1.

TABLE 1

Statistics of the validation data used in the study

| Number of pullbacks | 103 |
| --- | --- |
| Number of Patients | 72 |
| Number of Images | 8332* |
| Number of Stent Struts | 71881* |
| Percentage of malapposed struts | 5.7% |
| Percentage of struts with 0-0.1 mm tissue coverage | 78.1% |
| Percentage of struts with 0.1-0.2 mm tissue coverage | 12.2% |
| Percentage of struts with >0.2 mm tissue coverage | 4.0% |

*The number of images and struts are those analyzed by human expert analysts. The total numbers present in the pullbacks are much more.

There are in total more than 8000 manually analyzed images from 103 pullbacks from 72 patients. The data range from baseline to follow-up cases at different time points (note that the true number of images containing stent struts from the 103 pullbacks is more than 10,000, but because of time constraints, not every image was analyzed by human experts). In order to represent the widest possible range of cases that may be encountered in a clinical setting, no images were excluded from the data set for any reason. In particular, in each pullback, every image that had been analyzed by human experts was included in the validation. Therefore, images with different intensity, contrast, collected by different machines and with different artifacts commonly seen in clinical imaging, were included in this large validation set.

B. Gold Standard

For our purposes, there are two limitations of strut detection by human expert analysts (FIG. 6). First, analysts marked the front edge, instead of the center, of the strut bloom for analysis. From the perspective of OCT image formation, it is known that the actual strut front surface is the center of the point spread function, and should be near the center of the bloom. (To account for this, analysts routinely add a constant offset for strut-level analyses). Nevertheless, the mark that was obtained from manually analyzed images is placed on the front of the bloom. Because of this, to determine whether an automatically detected strut and a manually detected strut coincide, the distance between centroids of the strut markings need to be within a distance tolerance along the A-line. Using the same 342 struts (2 pullbacks) analyzed by two analysts with one marking the strut bloom center, and one marking the bloom front edge, the distance was determined to be 108 μm, within which the two analysts reached an agreement of 99% in detecting all the struts. Second, analysts did not mark every strut in a frame (FIG. 6) (this is true for almost all cases). In fact, they only marked struts having both a bright reflection and a dark shadow. This criterion was established so as to minimize inter-observer variations in strut-level analysis. However, it is quite common to find image evidence of struts without bright reflections due to an obliquely incident illumination angle. Because these are indeed true stent struts and are necessary for accurate stent area quantification, our algorithm was designed to include them. As a result, the automatic method disclosed herein will find many struts not identified as bright struts by analysts, resulting in apparently false positives. It is expected that the measured precision of the systems and methods disclosed using this "biased" gold standard should be significantly underestimated.

C. Training and Evaluation Studies

To evaluate automated stent strut detection, results obtained using methods disclosed herein were compared to results to gold standard detection and collected true positives (TP), false positives (FP), and false negatives (FN). True negatives (TN) are not informative as one might consider almost all non-strut pixels in the image as TN. As metrics of the accuracy of the automated detection system, recall (sensitivity) and precision are computed as follows:

$$\text{Recall}=TP/(TP+FN) \quad \text{Precision}=TP/(TP+FP)$$

First, the effect of the size of the training data set on the Bayesian classification stage of the algorithm was evaluated. FIG. 7 depicts graphs that illustrate the effect of the size of the training data set on the performance of Bayesian classification. In the example of FIG. 7, the testing data are a subset of randomly selected 10 pullbacks from the entire validation data set (978 images). Using the selected 10 pullbacks from the validation data, the performance of the method was tracked by varying the training data size from 1, 3, 5, 10, 15, 20, 30, 40, to 50 pullbacks. To isolate analysis of this step, the en face processing was excluded from this experiment, but instead simply classified the strut locations using the Bayes decision rule (P>0.5).

Second, the accuracy of the en face stent mesh segmentation was assessed. For this purpose, the automatic segmentation was compared to the manually segmented stent wires by a human expert in the en face view in a subset of 18 pullbacks (2251 images) using Dice's coefficient. To demonstrate that the algorithm is applicable to different stent designs, two different, yet representative types of stents were evaluated. The first type is Xience V stent (n=15), which is the most commonly used stent type is both the U.S. and around the world. It has longitudinal bridges linking adjacent circumferential wires. The second type is Nobori stent (n=3), in which adjacent circumferential wires are directly connected at junctions. Most of the stents used nowadays have similar shapes to these examples.

The major parameters equipped in the algorithm were then evaluated. The major free parameters are the weighting constants μ and λ used in the objective function (4), and the deformation constraint T in (5). Since (4) is a linear function, the parameters are estimated using a linear classifier such as single-layer perceptron from the training data. For this task, the classification is between strut pixels and non-strut pixels in the same A-line. It was determined μ=−0.4 and λ=0.3. T was determined by selecting the threshold within which 99% of the analyst-marked struts from the training data satisfy the constraint. This value was found to be about 0.3 mm.

With the optimized parameters, the performance of the entire algorithm was assessed to detect strut locations using all the human analyzed validation data. Results were also presented stratified by degree of neointima coverage. In all cases, the data used for training were different from the data used for validation.

Finally, quantitative stent areas derived from automatically detected struts by our algorithm were compared to those from manual analysis using the commercial software. Both correlation and Bland-Altman plots were used to assess agreement, as shown in FIG. 11. Other area measurements were not evaluated because the ground truth numbers of these measurements were not recorded in the datasets due to the limitation of the commercial software.

Example Results

A. Bayesian Classification Affected by the Training Data Size

FIG. 7 shows the performance of the method for detecting struts as a function of training data size. Even with a small number of pullbacks (e.g., 5 or 10), the number of struts is quite large, and the performance approaches that obtained with many more training data. At about 20 pullbacks, the performance of the method reaches a stable plateau. For the following studies, 20 pullbacks were as the training data size.

B. En Face Stent Mesh Segmentation

Figure 8:
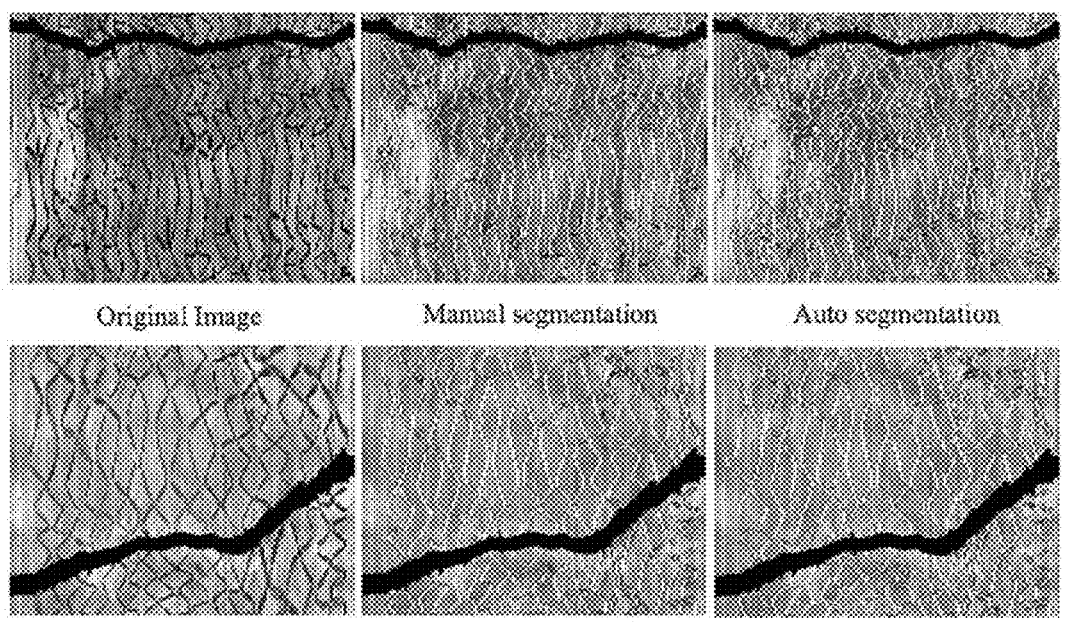
FIG. 8 depicts images demonstrating an example of en face stent segmentation results for two types of stents.

FIG. 8 illustrates examples of stent mesh segmentation in two stents with different designs. In both cases, MST-STENT performs well with an overall accuracy of DSC=0.87±0.04 (Dice's coefficient). But it achieved a higher accuracy with Nobori stents (DSC=0.92±0.06) than with Xience V stents (DSC=0.86±0.02). An example of the stent mesh search is illustrated in supplementary video 1.

C. Validation of Stent Strut Detection in a Large Clinical Data Set

FIGS. 9a, 9b and 9c illustrate examples of performance of the stent strut detection in 8332 clinical images from 103 pullbacks. As the gold standard is "biased" that not every strut was analyzed manually, the actual precision of the method is expected to be significantly underestimated. FIGS. 9a and 9b demonstrate recall and precision metrics for struts with different thickness of neointima coverage, respectively. These metrics are derived on a frame-by-frame basis. Tissue coverage was determined by the average thickness of all struts in a frame. The numbers under the bars indicate the number of images in each category. FIG. 9c depicts overall performance using all the images. Here the metrics are derived on a pullback-by-pullback basis.

Figure 9:
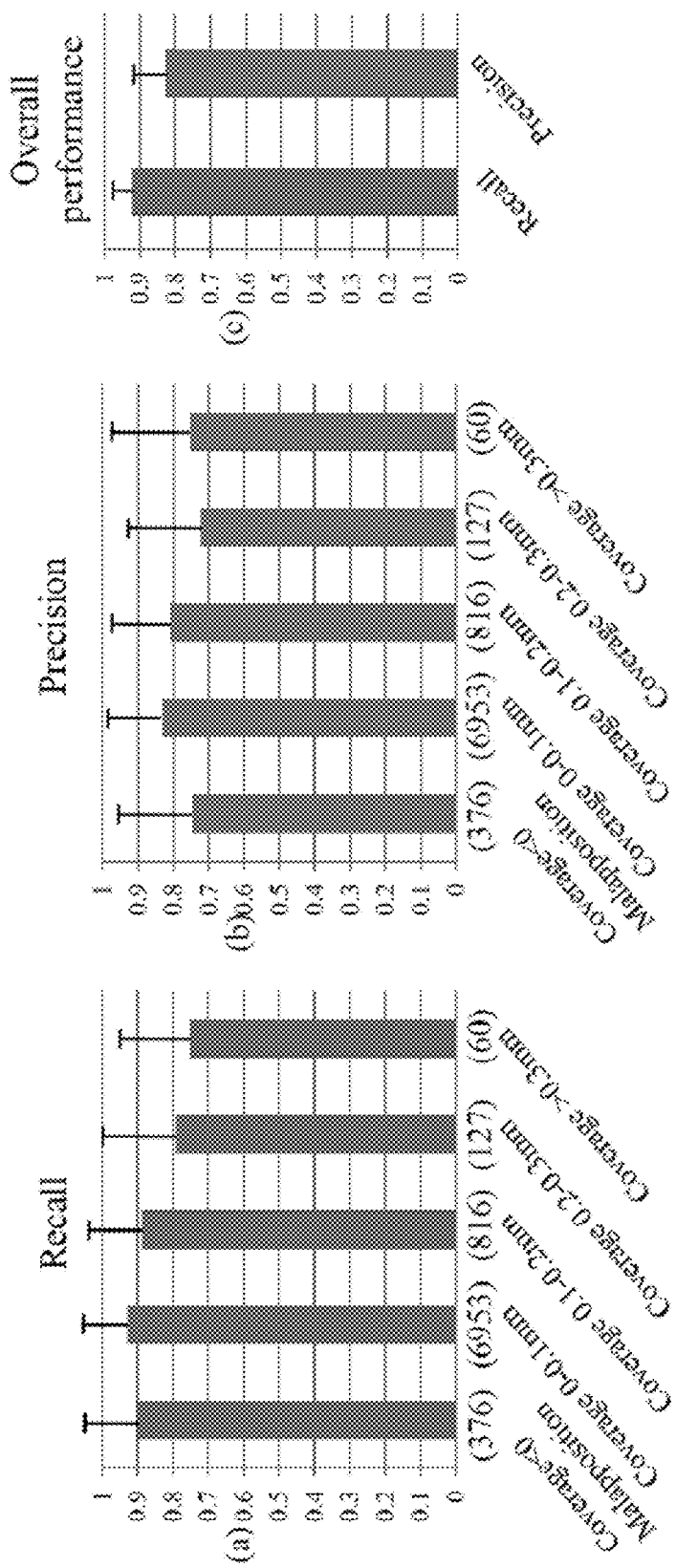
FIGS. 9a, 9b and 9c are graphs demonstrating examples of performance metrics associated with stent strut detection.

FIG. 9 shows strut detection statistics stratified by neointima coverage thickness. The algorithm achieved higher recall in struts with no or thin coverage, as compared to struts with thick coverage. Malapposed struts can be detected with a high recall (0.90±0.14), although with a reduced precision (0.75±0.19). Reduced precision for malapplosed corresponds to false positives from residual blood or struts which were just not marked by experts. The precision of the algorithm in cases with >0.3 mm tissue coverage is high despite its lower recall, and this is mainly because the detected false positives were also fewer. Overall, our method demonstrated 0.91±0.04 recall, and 0.84±0.08 precision. The actual performance is expected to be better than these numbers as experts did not always mark struts which were not bright (see, e.g., FIG. 6).

Figure 10:
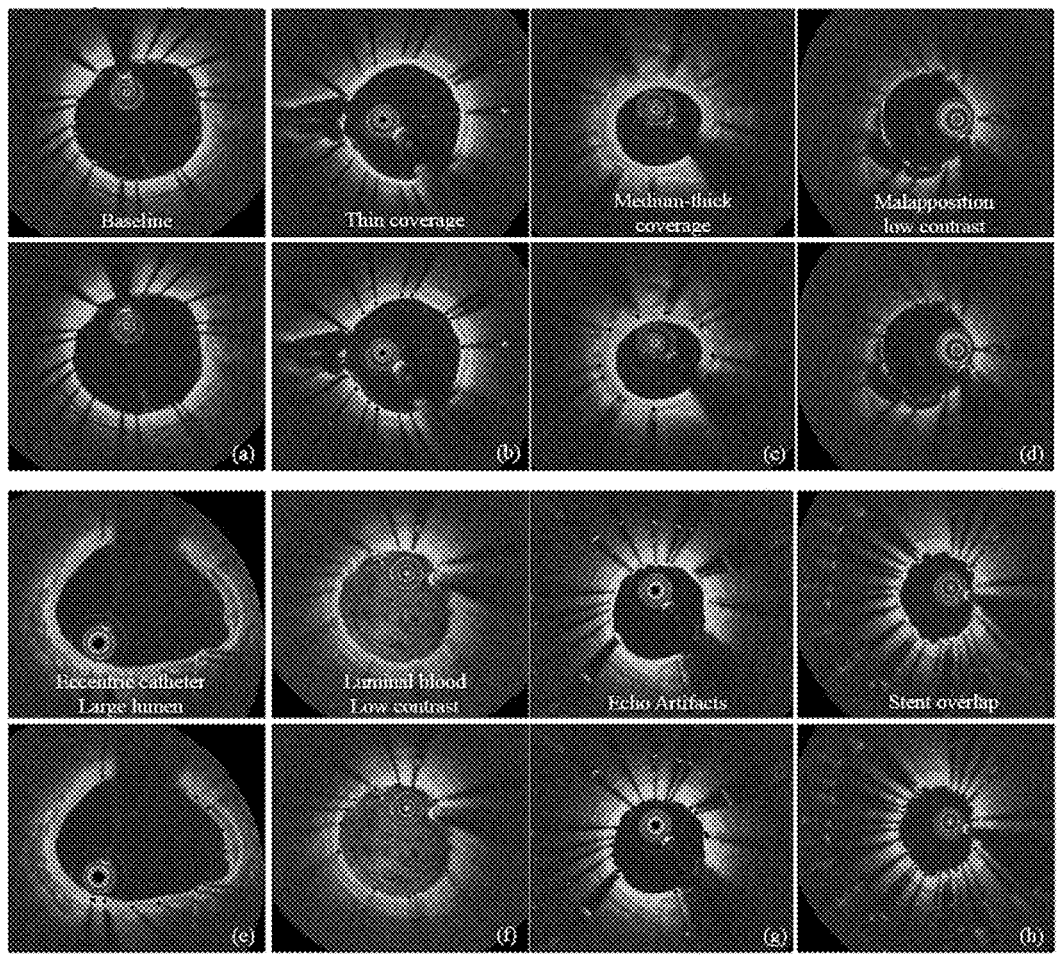
FIGS. 10a-10h illustrates examples of automated stent strut detection in cases with different amounts of neointima coverage, images of varying quality and in the presence of various artifacts.

FIGS. 10a-10h illustrate examples of automated stent strut detection in cases with different amounts of neointima coverage, images of varying quality and in the presence of various artifacts. FIGS. 10a-10h demonstrate the robust performance of the presented method in images of varying quality and in the presence of various artifacts. For example, FIGS. 10a-10d show struts with different thickness of tissue coverage (including negative coverage, i.e., malapposition). FIG. 10e shows an image acquired by an eccentrically positioned catheter, and the signatures of struts between 2 to 4 o'clock are very weak. But the algorithm was still able to detect them. FIG. 10f illustrates that the method can correctly detect the struts in images with very low contrast, which are quite common clinically and are usually due to residual luminal blood or blood inside the catheter. FIG. 10g shows that echo artifacts (bright multiple reflections in A-lines) do not affect the detection of the actual struts. FIG. 10h illustrates an example where two stents were implanted overlapping in the same artery, which again can be handled well by the method.

Automatically derived stent areas correlate well (r=0.99) with areas determined by analysts. A Bland-Altman plot indicates a bias with analysts giving smaller areas than the automated method. Stent area may be underestimated in the manual analysis because the stent contour was reconstructed from the front edge of the bloom without correction. The algorithm generated greater errors for those stents with larger areas as the struts were away from the catheter and were out of focus and were more difficult to detect.

D. 3-D Visualization

FIG. 12 illustrates 3-D reconstructions of an implanted stent from an intracoronary OCT pullback. The vessel was volume-rendered in orange, and the segmented stent was rendered in silver white. The voxels inside the lumen boundary were not rendered. FIG. 12a demonstrates stent rendering using only manually-marked struts in 2-D cross-sectional frames. All possible struts were segmented by an analyst, and confirmed by a second observer. This manual segmentation is too sparse to make a complete stent mesh in 3D. For better visualization, only half the vessel is shown. FIG. 12b demonstrates using en face projection processing, and mapping back to 2-D frames, which results in the 3-D stent being very well visualized. In FIG. 12c depicts a 3D example in a fly-though view demonstrating malapposed struts at 152. The dark band along the vessel is the region blocked by the guide wire.

For visualization, all the struts of a pullback were marked by an experienced analyst manually and confirmed by a second observer. Compared to manual detection (FIG. 12a), the automated method, especially en face processing, generated a more complete stent mesh for visualization (FIG. 12b). Due to the resolution from OCT imaging, the visualization can also compute and specify the distance between the stent and the lumen wall, thereby quantifying the malapposition shown at 152 in FIG. 12c. Additionally, the automated systems and methods disclosed herein are sufficiently fast that they can be considered feasible for live-time, clinical use.

In view of the foregoing, it will be appreciated that systems and methods disclosed herein provide a novel 3-D method for automated stent strut detection in intravascular OCT (e.g., IVOCT pullbacks). The approach disclosed herein may utilize both Bayesian network and graph search techniques, and has been proven to be effective and robust by analyzing a large data set collected in clinical environments.

The knowledge of OCT image formation has been leveraged to represent the structure of the Bayesian network for stent strut detection. Because the network structure is consistent with human logic and captures the intrinsic causal relationships between variables, it is associated with lower risks of over-training or poor generality. Additionally, the Bayesian network explicitly characterizes the probability of strut presence, and this provides greater flexibility and adaptability than binary classifiers.

This disclosure also provides a novel approach for stent detection by processing an en face projection image synthesized from the entire OCT sequence. This approach is dramatically different from previous approached where stent detection is performed in a frame-by-frame manner. Using 3-D mesh shape for stent strut detection is a hard problem because of the diverse range of stent designs that are implanted in patients. The proposed method based upon minimum spanning tree is the first real attempt to use the continuity of stent wires in 3-D to aid strut detection. Results are encouraging. The method assumes little knowledge about the design of a particular type of stent, and searches for the optimal stent mesh purely based on image data. This offers great generality and convenience for practical usage because analysts can blindly apply the algorithm without the need to specify the stent type for each pullback.

There are two additional advantages of performing stent mesh segmentation in the en face view. First, it can greatly help 3-D visualization of the entire stent, such as shown in FIG. 12b. 3-D visualization of stents can provide important morphological information for clinical diagnosis, such as malapposition and stent fracture. Longitudinal vessel features are significantly under-sampled by current commercial OCT systems (e.g., about 200 μm between frames for the C7-XRTM, St. Jude Medical Inc.) as compared to the axial and transverse resolutions 15-20 μm, with the pixel size smaller than the optical resolution. If only clear struts are detected in 2-D frames, there are gaps and the 3-D reconstruction suffers. En face processing thus can help pick up many ambiguous struts that are unclear in single frames, but are indeed real struts by combining neighboring slice information (see, e.g., FIG. 2). Although these ambiguous struts are usually not included for quantification, they are beneficial for 3-D visualization. The second advantage is that manual post-correction of a wrongly segmented wire in the en face projection view can be more efficient than in individual frames. Analysts can use an algorithm such as live-wire or intelligent scissors to add or delete some wires. This is equivalent to the analyst correcting stent struts in several frames at once. In comparison, single-frame based methods require the operators to manually correct the locations for every wrongly determined strut, which is time intensive.

In addition to using graph search to detect those A-lines containing struts, graph search was used to determine the depth location of struts. This incorporates the roughly cylindrical shape of the stent in global processing. These high-level approaches allow cross-sectional frames with very sparse struts (usually at junctions) to be localized accurately. Additionally, as for non-metal (i.e., bioabsorbable) stents, the principles of Bayesian inference, stent wire segmentation in the en face projection view and simultaneous depth localization of all struts can all be applied.

As can be appreciated by those skilled in the art, portions of the invention may be embodied as a method, data processing system, or computer program product (e.g., a non-transitory computer readable medium having instructions executable by a processor). Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable non-transitory computer-readable medium may be utilized including, but not limited to, static and dynamic storage devices, hard disks, optical storage devices, and magnetic storage devices.

Certain embodiments are disclosed herein with reference to flowchart illustrations of methods, systems, and computer program products. It can be understood that blocks of the illustrations, and combinations of blocks in the illustrations, can be implemented by computer-executable instructions. These computer-executable instructions may be provided to one or more processor cores of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in a non-transitory computer-readable medium that can direct a computer or other programmable data processing apparatus (e.g., one or more processing core) to function in a particular manner, such that the instructions stored in the computer-readable medium result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks or the associated description.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method comprising:
   storing three-dimensional image data comprising a sequential series of image frames acquired intravascularly via an optical coherence tomography (OCT) apparatus;
   analyzing the image data to compute a probability estimate of stent presence at support positions appearing in an A-line using a Bayesian network;
   identifying stent strut locations in three-dimensional space based on the computed probability estimate of stent presence;
   generating a two-dimensional en face image based on the stored image data;

segmenting the en face image to determine strut locations by using a graph search algorithm; and using the strut locations from the en face image to reinforce the computed probability estimate of stent presence.

2. The method of claim 1, wherein the graph search algorithm further comprises a minimum spanning tree method.

3. The method of claim 2, further comprising converting the strut locations of the en face image into an en face stent mesh structure, the en face stent mesh structure being used to reinforce the computed probability estimate of stent presence.

4. The method of claim 1, wherein the analyzing further comprises
computing an initial estimate of strut depth;
identifying high confidence struts based on the initial estimate of strut depth;
determining a refined estimate of strut depth for the high confidence struts;
interpolating strut depths at other possible locations based on the refined estimate of strut depth for the high confidence struts to provide interpolated strut depth for a subset of the other possible locations; and
determining a final probability estimate of strut presence.

5. The method of claim 1, further comprising determining strut depth locations in the A-line.

6. The method of claim 5, wherein determining the strut depth locations further comprises using a graph cut method.

7. The method of claim 6, wherein determining the strut depth locations comprises localizing the strut depths based upon the image data that is acquired during a pullback of the apparatus with respect to the stent.

8. The method of claim 1, further comprising computing a percentage of stent struts with tissue coverage.

9. The method of claim 1, further comprising computing at least one measurement based on the identified stent strut locations.

10. The method of claim 9, wherein the at least one measurement that is computed comprises at least one of a stent area, a malapposition area of the stent or a neointima area of the stent.

11. The method of claim 9, wherein the at least one measurement comprises at least one of a coverage thickness for at least one strut, a malapposition distance for a pair of struts.

12. The method of claim 1, further comprising:
using the graph search algorithm to detect a set of A-lines containing struts, and
using a graph cut method to determine a depth location of the stent struts.

13. The method of claim 1, wherein the stent comprises a metallic stent, the method further comprising analyzing the image data to evaluate properties of the metallic stent.

14. The method of claim 13, wherein the analyzing the image data to evaluate properties of the metallic stent comprises comparing properties of the metallic stent relative to properties of stents with different designs.

15. The method of claim 1, wherein the stent comprises a bioabsorbable stent, the method further comprising analyzing the image data to evaluate properties of the bioabsorbable stent.

16. The method of claim 15, wherein the analyzing further comprises performing comparative analysis of the properties of the bioabsorbable stent relative to properties of other stents.

17. The method of claim 1, wherein the OCT apparatus is one of a time-domain OCT apparatus, a spectral-domain OCT apparatus and a swept-source OCT apparatus.

18. The method of claim 1, wherein the analyzing further comprises analyzing a plurality of sets of the image data, the plurality of sets of the image data being acquired for the OCT apparatus operating based on different operating and/or control parameters.

19. The method of claim 18, wherein the different operating and/or control parameters comprise at least two of different rotation speed, different pullback speed, axial and transversal resolution.

20. An optical coherence tomography system comprising:
an optical coherence tomography (OCT) apparatus to provide three-dimensional OCT image data based on a sequential series of images acquired by an OCT probe intravascularly;
a signal processing system that includes image analysis program instructions to:
analyze the image data to compute a probability estimate of stent presence at support positions appearing in an A-line using a Bayesian network; and
reinforce the computed probability estimate of stent presence by:
generating a two-dimensional en face image based on the image data;
segmenting the en face image to determine strut locations by using a graph search algorithm; and
using the determined strut locations from the en face image to reinforce the computed probability estimate of stent presence; and
an output generator to identify stent strut locations based on the computed probability estimate of stent presence.

21. The system of claim 20, wherein the image analysis program instructions comprises depth locator program instructions to
compute an initial estimate of strut depth;
identify high confidence struts based on the initial estimate of strut depth;
determine a refined estimate of strut depth for the high confidence struts;
interpolate strut depths at other possible locations based on the refined estimate of strut depth for the high confidence struts to provide interpolated strut depth for a subset of the other possible locations; and
determine a final probability estimate of strut presence.

22. The system of claim 20, further comprising a user interface to set control parameters for the system to control at least one of a probe rotation speed, pullback speed, axial and resolution of the OCT image.

23. The system of claim 20, wherein the image analysis program instructions comprises measurement calculator program instructions to compute at least one measurement that includes a stent area, a malapposition area of the stent, a neointima area of the stent, a coverage thickness for at least one strut, or a malapposition distance for a pair of struts.

24. The system of claim 23, wherein the output generator superimposes the computed measurement on a graphical image of the stent superimposed on an image of a vessel.

25. The system of claim 20, wherein the image analysis program instructions further comprise instructions to convert the strut locations of the en face image into an en face stent mesh structure, the en face stent mesh structure being used to reinforce the computed probability estimate of stent presence.

* * * * *